United States Patent
Donde

(10) Patent No.: US 7,169,807 B2
(45) Date of Patent: Jan. 30, 2007

(54) 10-HYDROXY-11-DIHYDROPROSTAGLANDIN ANALOGS AS SELECTIVE EP4 AGONISTS

(75) Inventor: Yariv Donde, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 420 days.

(21) Appl. No.: 10/821,705

(22) Filed: Apr. 9, 2004

(65) Prior Publication Data

US 2005/0228185 A1    Oct. 13, 2005

(51) Int. Cl.
A61K 31/38    (2006.01)
C07D 333/56   (2006.01)

(52) U.S. Cl. ........................................ 514/443; 549/58
(58) Field of Classification Search ................ 549/58; 574/443
See application file for complete search history.

(56) References Cited

U.S. PATENT DOCUMENTS

| | | | |
|---|---|---|---|
| 3,931,297 A | 1/1976 | Crabbe | |
| 4,166,452 A | 9/1979 | Generales | |
| 4,171,375 A | 10/1979 | Caton et al. | |
| 4,256,108 A | 3/1981 | Theeuwes | |
| 4,265,874 A | 5/1981 | Bonsen et al. | |
| 4,994,274 A | 2/1991 | Chan et al. | |
| 5,028,624 A | 7/1991 | Chan et al. | |
| 5,034,413 A | 7/1991 | Chan et al. | |
| 5,446,041 A | 8/1995 | Chan et al. | |
| 5,688,819 A | 11/1997 | Woodward et al. | |
| 6,353,000 B1 | 3/2002 | Sallee et al. | |
| 6,552,067 B2 | 4/2003 | Cameron et al. | |
| 6,586,463 B2* | 7/2003 | deLong et al. | 514/443 |
| 6,586,468 B1 | 7/2003 | Maruyama et al. | |
| 6,767,920 B2* | 7/2004 | Burk et al. | 514/443 |
| 6,875,787 B2* | 4/2005 | Donde | 514/385 |
| 6,884,896 B2* | 4/2005 | Saitoh et al. | 549/58 |
| 7,015,243 B2* | 3/2006 | Old et al. | 514/443 |

FOREIGN PATENT DOCUMENTS

| | | |
|---|---|---|
| BE | 850348 | 7/1977 |
| DE | 2701455 | 1/1977 |
| DE | 2752523 | 11/1977 |
| ES | 409167 | 3/1971 |
| FR | 2162213 | 12/1972 |
| FR | 2338244 | 1/1976 |
| FR | 2408567 | 11/1977 |
| GB | 1405301 | 9/1975 |
| JP | 52087144 | 7/1977 |
| JP | 53065854 | 6/1978 |
| NL | 7700272 | 1/1977 |
| SE | 7700257 | 7/1977 |

OTHER PUBLICATIONS

U.S. Appl. No. 10/365,369, filing date Feb. 11, 2003.

Adam et. al. *Spectral and Chemical Properties of Dimethyldioxirane as Determined by Experiment and ab Initio Calculations*; J. Org. Chem. 1987, 52, 2800.
Bezuglov, et. al., "Synthesis and Biological Evaluation of Novel Amides of Polyunsaturated Fatty Acids with Dopamine", Bioorganic & Medicinal Chemistry Letters 11 (2001), 447-449.
Bito, L.Z. *Biological Protection with Prostaglandins*, Cohen, M.M., ed., Boca Raton, Fla, CRC Press Inc., 1985, pp. 231-252.
Bito, L.Z., *Applied Pharmacology in the Medical Treatment of Glaucomas* Drance, S.M. and Neufeld, A.H. eds., New York, Grune & Stratton, 1984, pp. 477-505.
Bito, L.Z., Prostaglandins Old concepts and new perspectives, *Arch Ophthalmol*, vol. 105, pp. 1036-1039 (1987).
Carey, Francis A., Organic Chemistry, New York: McGraw-Hill Book Company 1987, p. 63.
Nilsson, S., et al., PGF2 increases uveoscleral outflow, *Invest Ophthalmic Vis Sci.* (suppl) 284 ARVO Abstracts, 1987.
Remington's Pharmaceutical Sciences, Mack Publishing Company, Easton, Pa., 16th Edition, 1980.
Siebold, et al., Esterfied prostaglandin shows 'potent' promise, *Prodrug*, (5) 3 (1989).

* cited by examiner

Primary Examiner—Deborah C. Lambkin
(74) Attorney, Agent, or Firm—Brent A. Johnson; Robert J. Baran; Martin A. Voet

(57) ABSTRACT

A compound comprising

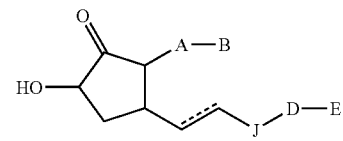

or a pharmaceutically acceptable salt or a prodrug thereof, wherein
the dashed line represents the presence or absence of a double bond;
J is C=O or CHOH;
A is —(CH$_2$)$_6$—, or cis —CH$_2$CH=CH—(CH$_2$)$_3$—, wherein 1 or 2 carbons may be substituted with S or O;
B is CO$_2$H, or CO$_2$R, CONR$_2$, CONHCH$_2$CH$_2$OH, CON(CH$_2$CH$_2$OH)$_2$, CH$_2$OR, P(O)(OR)$_2$, CONRSO$_2$R, SONR$_2$, or

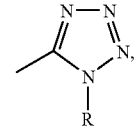

R is H, C$_{1-6}$ alkyl;
D is —(CH$_2$)$_n$—, —X(CH$_2$)$_n$, or —(CH$_2$)$_n$X—, wherein n is from 0 to 3 and X is S or O; and
E is an aromatic or heteroaromatic moiety having from 0 to 4 substituents, said substituents each comprising from 1 to 6 non-hydrogen atoms is disclosed herein. Methods, compositions, and medicaments related thereto, as well as experimental results showing prostaglandin EP4 selective agonist activity for certain compounds disclosed herein, are also disclosed.

24 Claims, 2 Drawing Sheets

Scheme 1
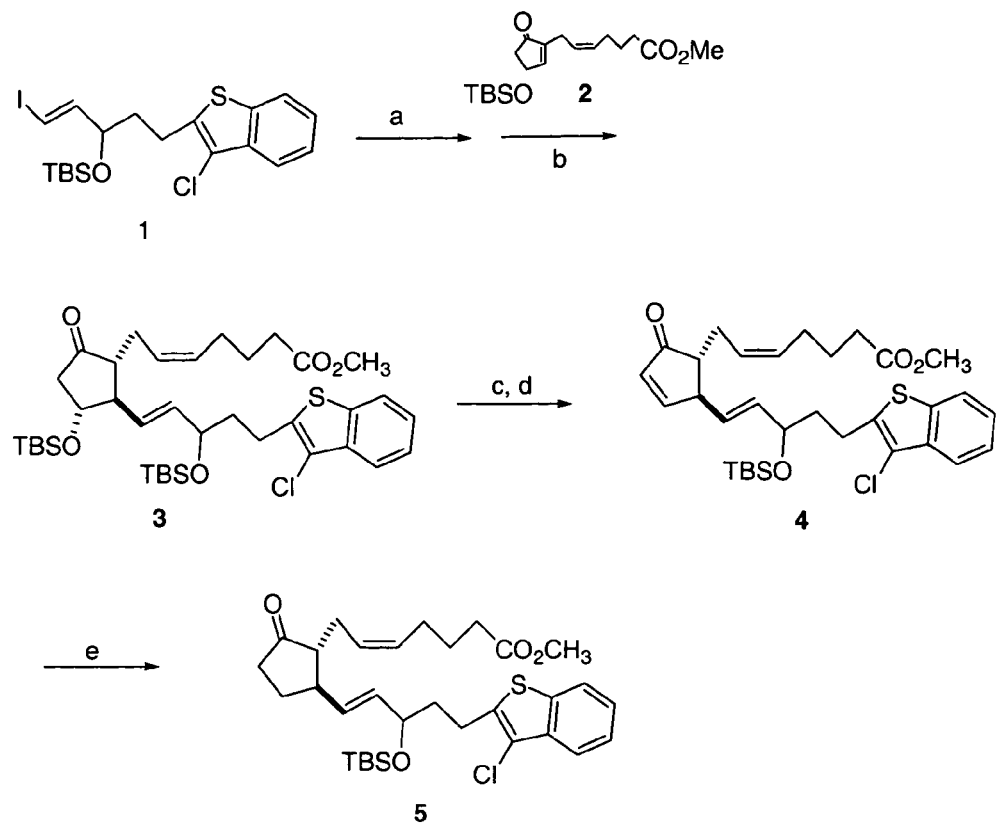
(a) *t*-BuLi, THF -78 °C; 2-ThienylCuCNLi, THF -78 °C; (b) 2, THF -78 °C; (c) HOAc, H$_2$O, THF 70 °C; (d) TBSOTf, 2,6-lutidine, CH$_2$Cl$_2$; (e) [Ph$_3$PCuH]$_6$.

Scheme 2
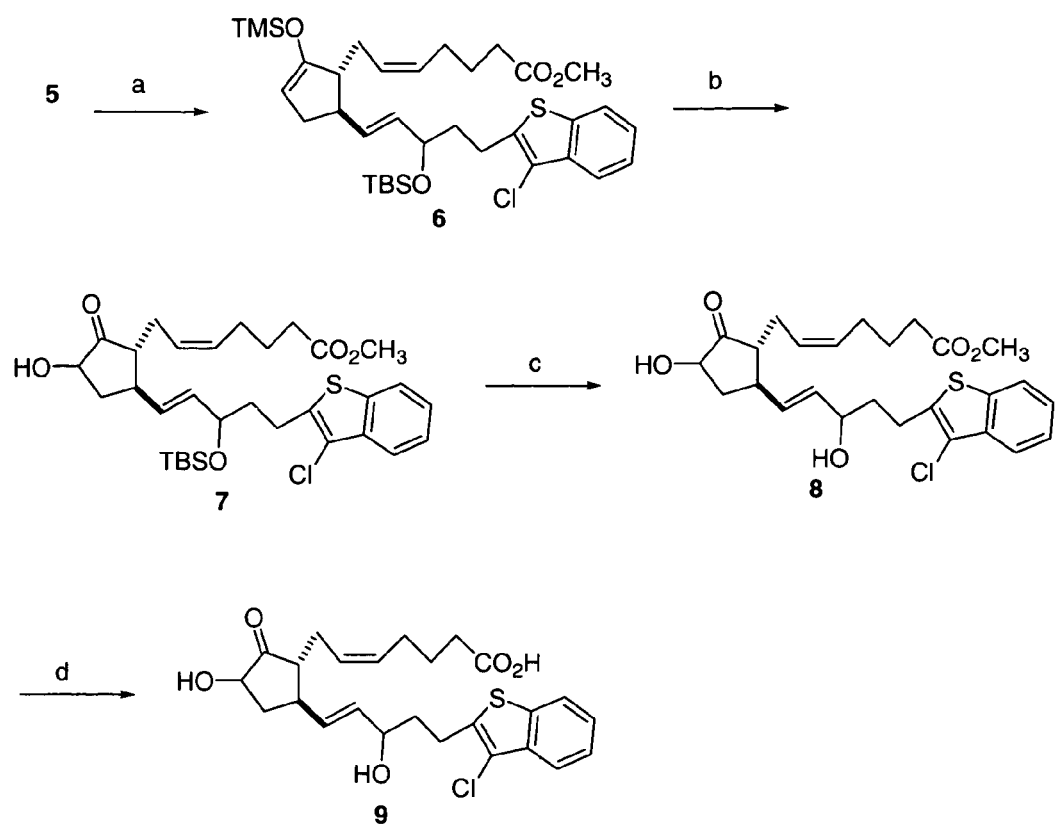
(a) LDA, TMSCl; (b) dimethyldioxirane; PPTS THF/$H_2O$ (c) HF-pyridine; (d) Rabbit Liver Esterase.

10-HYDROXY-11-DIHYDROPROSTAGLANDIN ANALOGS AS SELECTIVE EP4 AGONISTS

BACKGROUND OF THE INVENTION

1. Field of the Invention

This invention relates to compounds which are useful as therapeutic agents. Among other potential uses, these compounds are believed to have properties which are characteristic of prostaglandins.

2. Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

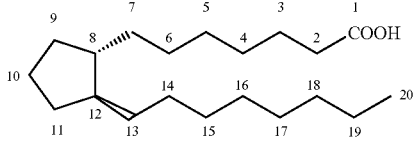

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas Drance*, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et. al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of United States patents assigned to Allergan, Inc. prostaglandin esters with increased ocular hypotensive activity accompanied with no or substantially reduced side-effects are disclosed. Some representative examples are U.S. Pat. No. 5,446,041, U.S. Pat. No. 4,994,274, U.S. Pat. No. 5,028,624 and U.S. Pat. No. 5,034,413 all of which are hereby expressly incorporated by reference.

U.S. Pat. No. 5,688,819, commonly assigned to Allergan, Inc., and incorporated herein by reference discloses compounds known as prostamides. Prostamides are distinguished from prostaglandins in that the oxygen which is bonded to carbonyl group is replaced by a nitrogen bearing substituent. Those skilled in the art will readily recognize that this replacement significantly alters several electronic and steric properties of an important structural feature in the biological molecule. Significantly, it is commonly believed in the art that resonance between the nitrogen lone pair and the carbonyl π-bond is significantly greater than resonance between the carbonyl group and an oxygen lone pair in a carboxylic ester or a carboxylic acid. This belief is supported by the well established experimental observation that the nitrogen atom in an amide is planar, as opposed to the pyramidal geometry of an amine. Thus, the commonly accepted belief in the art is that the nitrogen atom of an amine is $sp^3$ hybridized, while nitrogen atom of an amide is $sp^2$ hybridized, with the bonded electrons occupying the $sp^2$ hybrid orbitals and the nonbonded electron pair occupying a p orbital to allow for conjugation with the carbonyl π system. By contrast, the hybridization, bonding, and geometry of the electrons of the oxygen atom in water and alcohols are very similar to those of carboxylic acids or carboxylic esters.

The increased resonance between the nitrogen and the carbonyl group in the amide confers several unique properties to the molecule. First, it is well known in the art that hydrolysis of amides is at least two orders of magnitude slower than the hydrolysis of esters (see, for example, Francis A. Carey, Organic Chemistry, New York: McGraw-Hill Book Company, 1987, p. 779). Thus, hydrolysis of amides in vivo is slowed to such an extent that a prostamide cannot be considered to be a prodrug of a prostaglandin. Second, the increased resonance significantly increases the barrier to rotation about the nitrogen-carbonyl sigma bond relative to the analogous rotational barrier associated with esters and carboxylic acids. Thus, a prostamide has a sterically significant, stable, rigid group replacing the oxygen atom of the prostaglandin. This significant steric difference will have a significant effect in binding to a number of receptor sites since geometry is important for many receptor sites. Since the carboxylic acid group of a prostaglandin is a polar, ionizable, group, with four potential hydrogen bond receiving electron pairs, and in the case of the protonated acid, one potential hydrogen bond donor, it is reasonable for a person of ordinary. skill in the art to believe that this functional group will be important to the binding of the molecule to a number of receptors. It follows that changing the resonance properties, the hybridization of the bonding and nonbonding electrons, the geometry of the nitrogen atom, the number of available hydrogen bonding sites, and the electronegativity of the of the nitrogen relative to oxygen, will confer significantly different biological properties to prostamides relative to prostaglandins.

Recently, it is becoming more commonly accepted in the art that amides have distinct properties over carboxylic acids. For example, it has been shown that anandamide, a common amide of arachidonic acid, has significant biological activity that arachidonic acid does not. Other work has also been done to show that amides have distinct activity as compared to carboxylic acid, which has caused some in the field to classify fatty acid amides as "a new family of biologically active lipids" (Bezuglov, et. al., "Synthesis and Biological Evaluation of Novel Amides of Polyunsaturated Fatty Acids with Dopamine", Bioorganic & Medicinal Chemistry Letters 11 (2001), 447–449).

It has been shown that prostamides have pronounced effects on smooth muscle and are potent ocular hypotensive agents. Additionally, prostamides cause significantly lower ocular surface hyperemia than prostaglandins. One prostamide exemplary of the these effects is bimatoprost, which is marketed by Allergan, Inc. under the trade name Lumigan®, which has the structure shown below.

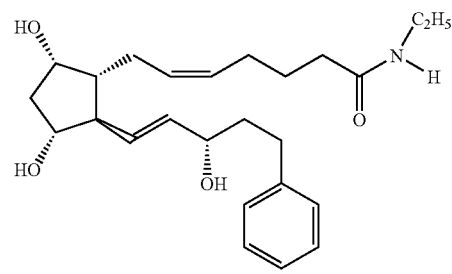

Although prostamide compounds have activity which is distinct from prostaglandins, they have many similar structural features. While not intending to be bound in any way by theory, it is believed that the structural similarity arises because prostamides are biosynthesized from N-arachidonyl ethanolamide whereas prostaglandins are biosynthesized from the structurally related arachidonic acid. Thus, they have similar structural traits, but play physiologically distinct roles due to the unique differences between the amide and the acid or ester functional groups highlighted previously. For example, it is believed that the two classes of compounds are active at distinct receptors. Thus, it is believed that the prostamide and prostaglandin receptors recognize a similar geometry in terms of the basic ring and α- and ω-chain structure, or analogs thereof, but selectively distinguish between prostaglandin and prostamide compounds based upon the nitrogen or oxygen substitution at the carbonyl.

10-Hydroxyprostaglandin analogues, that is natural prostaglandin E compounds where the hydroxide is present on carbon 10 rather than carbon 11, are known in several patent documents including U.S. Pat. No. 4,171,375; U.S. Pat. No. 3,931,297; FR 2408567; DE 2752523, JP 53065854, DE 2701455, SE 7700257, DK 7700272, NL 7700272, JP 52087144, BE 850348, FR 2338244, FR 2162213, GB 1405301, and ES 409167.

Prostaglandin $EP_4$ selective agonists are believed to have several medical uses. For example, U.S. Pat. No. 6,552,067 B2 teaches the use of prostaglandin EP4 selective agonists for the treatment of "methods of treating conditions which present with low bone mass, particularly osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth in a mammal". U.S. Pat. No. 6,586,468 B1 teaches that prostaglandin EP4 selective agonists "are useful for the prophylaxis and/or treatment of immune diseases (autoimmune diseases (amyotrophic lateral sclerosis (ALS), multiple sclerosis, Sjoegren's syndrome, arthritis, rheumatoid arthritis, systemic lupus erythematosus, etc.), post-transplantation graft rejection, etc.), asthma, abnormal bone formation, neurocyte death, pulmopathy, hepatopathy, acute hepatitis, nephritis, renal insufficiency, hypertension, myocardial ischemia, systemic inflammatory syndrome, pain induced by ambustion, sepsis, hemophagocytosis syndrome, macrophage activation syndrome, Skill's diseases, Kawasaki diseases, burn, systemic granuloma, ulcerative colititis, Crohn's diseases, hypercytokinemia at dialysis, multiple organ failure, shock, etc. They are also connected with sleeping disorders and platelet coagulations, and therefore they are thought to be useful for these diseases."

BRIEF DESCRIPTION OF THE INVENTION

A compound comprising

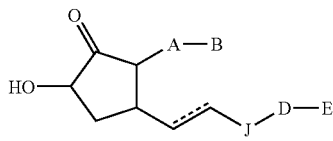

or a pharmaceutically acceptable salt or a prodrug thereof, wherein the dashed line represents the presence or absence of a double bond;

J is C=O or CHOH;

A is —(CH$_2$)$_6$—, or cis —CH$_2$CH=CH—(CH$_2$)$_3$—, wherein 1 or 2 carbons may be substituted with S or O;

B is CO$_2$H, or CO$_2$R, CONR$_2$, CONHCH$_2$CH$_2$OH, CON(CH$_2$CH$_2$OH)$_2$, CH$_2$OR, P(O)(OR)$_2$, CONRSO$_2$R, SONR$_2$, or

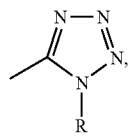

R is H, C$_{1-6}$alkyl;

D is —(CH$_2$)$_n$—, —X(CH$_2$)$_n$, or —(CH$_2$)$_n$X—, wherein n is from 0 to 3 and X is S or O; and E is an aromatic or heteroaromatic moiety having from 0 to 4 substituents, said substituents each comprising from 1 to 6 non-hydrogen atoms is disclosed herein.

Also disclosed herein are methods of treating diseases or conditions, including glaucoma, elevated intraocular pressure, and diseases related to the activity of a prostaglandin EP$_4$ receptor. Compositions and methods of manufacturing medicaments related thereto are also disclosed.

BRIEF DESCRIPTION OF THE DRAWING FIGURES

Schemes 1 and 2 illustrate one method of preparing the compounds disclosed herein.

DETAILED DESCRIPTION OF THE INVENTION

Several of the carbon atoms on these compounds are chiral centers. While not intending to limit the scope of the invention in any way, or be bound in any way by theory, it is believed that many compounds and pharmaceutically active salts or prodrugs thereof having the stereochemistry shown below are particularly useful.

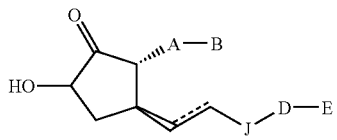

However, it is also advantageous if one of the bonds has the indicated stereochemistry, while the stereochemistry of other bond to chiral centers may vary. Thus, while not intending to limit the scope of the invention in any way, compounds comprising

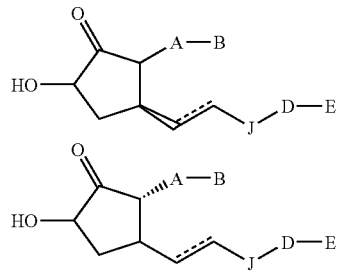

and pharmaceutically acceptable salts and prodrugs thereof, are particularly useful in the context disclosed herein.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper to toward the viewer" and the hatched wedge, indicated as a "dashed line", "represents a bond receding from the viewer."

In relation to the identity of A disclosed in the chemical structures presented herein, in the broadest sense, A is —(CH$_2$)$_6$—, or cis —CH$_2$CH=CH—(CH$_2$)$_3$—, wherein 1 or 2 carbons may be substituted with S or O. In other words, A may be —(CH$_2$)$_6$—, cis —CH$_2$CH=CH—(CH$_2$)$_3$—, or A may be a group which is related to one of these two moieties in that any carbon is substituted with S or O. For example, while not intending to limit the scope of the invention in any way, S may be an S substituted moiety such as one of the following or the like.

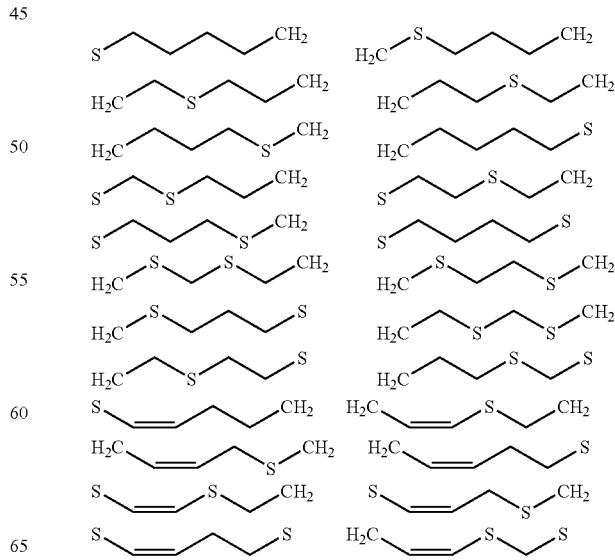

Alternatively, while not intending to limit the scope of the invention in any way, S may be an O substituted moiety such as one of the following or the like.

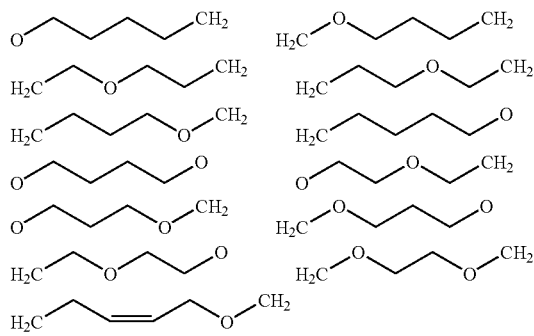

In other embodiments, A is —(CH$_2$)$_6$— or cis-CH$_2$CH=CH—(CH$_2$)$_3$— having no heteroatom substitution.

The term alkyl has the meaning generally understood by those skilled in the art and refers to linear, branched, or cyclic alkyl moieties. A "C$_{1-6}$ alkyl" moiety has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1–6 carbon atoms, etc. In compounds where B is CO$_2$R, CONR$_2$, CH$_2$OR, P(O)(OR)$_2$, CONRSO$_2$R, SONR$_2$, compounds wherein R is methyl, ethyl, or isopropyl, are specifically contemplated herein.

In relation to the identity of D, D is —(CH$_2$)$_n$—, —X(CH$_2$)$_n$, or —(CH$_2$)$_n$X—, wherein n is from 0 to 3 and X is S or O. In other words, while not intending to be limiting, D may be a bond, —CH$_2$—, —CH$_2$CH$_2$—, —CH$_2$CH$_2$CH$_2$—, S, O, —SCH$_2$—, —SCH$_2$CH$_2$—, —SCH$_2$CH$_2$CH$_2$—, —CH$_2$S—, —CH$_2$CH$_2$S—, —CH$_2$CH$_2$CH$_2$S—, —OCH$_2$—, —OCH$_2$CH$_2$—, —OCH$_2$CH$_2$CH$_2$—, —CH$_2$O—, —CH$_2$CH$_2$O—, or —CH$_2$CH$_2$CH$_2$O—. A person of ordinary skill in the art will understand that n is required to be an integer.

In relation to E, E is an aromatic or heteroaromatic moiety having from 0 to 4 substituents, said substituents each comprising from 1 to 6 non-hydrogen atoms. In other words, E can be an aromatic moiety such as phenyl, napthyl, etc, or E can be a heteroaromatic moiety such as thienyl, pyridinyl, furyl, benzothienyl, etc. Alternatively, E can be one of these aromatic or heteroaromatic moieties, which is substituted with from 1 to 4 substituents. The substituents comprise from 1 to 6 non-hydrogen atoms, in other words, there are from 1 to 6 atoms which are not hydrogen, any number of hydrogen atoms required to form the complete substituent. For example, a methyl substituent has 1 carbon atom and 3 hydrogen atoms. Other example substituents include other hydrocarbon moieties comprising from 1 to 6 carbon atoms including alkyl such as ethyl, propyl, isopropyl, butyl and isomers thereof, pentyl and isomers thereof, hexyl and isomers thereof; cyclic and unsaturated hydrocarbons having 1 to 6 carbon atoms; CO$_2$H and salts thereof; alkoxy up to C$_5$ such as methoxy, ethoxy, propoxy, isopropoxy, a butoxy isomer, or a pentoxy isomer; carboxylic acid esters; CN; NO$_2$; CF$_3$; F; Cl; Br; I; sulfonyl esters; SO$_3$H and salts thereof; and the like. These substituents may be in any reasonable position on the aromatic or heteroaromatic moiety. A person of ordinary skill in the art will understand that the number of substituents will be an integer.

In other words, while not intending to limit the scope of the invention in any way E can be chlorophenyl, dichlorophenyl, trichlorophenyl, tetrachlorophenyl, fluorophenyl, difluorophenyl, trifluorophenyl, tetrafluorophenyl, (trifluoromethyl)phenyl, di(trifluoromethyl)phenyl, tri(trifluoromethyl)phenyl, tetra(trifluoromethyl)phenyl, methylphenyl, dimethylphenyl, trimethylphenyl, tetramethylphenyl, methoxyphenyl, dimethoxyphenyl, trimethoxyphenyl, tetramethoxyphenyl, cyanophenyl, dicyanophenyl, tricyanophenyl, tetracyanophenyl, or can have mixed substituents such as chlorofluorophenyl, chloromethylphenyl, chloromethoxyphenyl, chloroflouromethylphenyl, etc. Similarly, while not intending to be limiting, other aromatic moieties could be chloronapthyl, dichloronapthyl, trichloronapthyl, tetrachloronapthyl, fluoronapthyl, difluoronapthyl, trifluoronapthyl, tetrafluoronapthyl, (trifluoromethyl)napthyl, di(trifluoromethyl)napthyl, tri(trifluoromethyl)napthyl, tetra(trifluoromethyl)napthyl, methylnapthyl, dimethylnapthyl, trimethylnapthyl, tetramethylnapthyl, methoxynapthyl, dimethoxynapthyl, trimethoxynapthyl, tetramethoxynapthyl, cyanonapthyl, dicyanonapthyl, tricyanonapthyl, tetracyanonapthyl, or can have mixed substituents such as chlorofluoronapthyl, chloromethylnapthyl, chloromethoxynapthyl, chloroflouromethylnapthyl, etc. Heteroaromatic moieties, could include, but are not limited to chloropyridinyl, dichloropyridinyl, trichloropyridinyl, tetrachloropyridinyl, fluoropyridinyl, difluoropyridinyl, trifluoropyridinyl, tetrafluoropyridinyl, (trifluoromethyl)pyridinyl, di(trifluoromethyl)pyridinyl, tri(trifluoromethyl)pyridinyl, tetra(trifluoromethyl)pyridinyl, methylpyridinyl, dimethylpyridinyl, trimethylpyridinyl, tetramethylpyridinyl, methoxypyridinyl, dimethoxypyridinyl, trimethoxypyridinyl, tetramethoxypyridinyl, cyanopyridinyl, dicyanopyridinyl, tricyanopyridinyl, tetracyanopyridinyl, or can have mixed substituents such as chlorofluoropyridinyl, chloromethylpyridinyl, chloromethoxypyridinyl, chloroflouromethylpyridinyl, etc. Similarly, while not intending to be limiting, other heteroaromatic moieties could be chlorobenzothienyl, dichlorobenzothienyl, trichlorobenzothienyl, tetrachlorobenzothienyl, fluorobenzothienyl, difluorobenzothienyl, trifluorobenzothienyl, tetrafluorobenzothienyl, (trifluoromethyl)benzothienyl, di(trifluoromethyl)benzothienyl, tri(trifluoromethyl)benzothienyl, tetra(trifluoromethyl)benzothienyl, methylbenzothienyl, dimethylbenzothienyl, trimethylbenzothienyl, tetramethylbenzothienyl, methoxybenzothienyl, dimethoxybenzothienyl, trimethoxybenzothienyl, tetramethoxybenzothienyl, cyanobenzothienyl, dicyanobenzothienyl, tricyanobenzothienyl, tetracyanobenzothienyl, or can have mixed substituents such as chlorofluorobenzothienyl, chloromethylbenzothienyl, chloromethoxybenzothienyl, chloroflouromethylbenzothienyl, etc.

In other embodiments E is an aromatic or heteroaromatic moiety having from 0 to 2 substituents, wherein said aromatic moiety is selected from the group consisting of phenyl, thienyl, benzothienyl, and napthyl, and said substituents are selected from the group consisting of methyl, methoxy, chloro, and fluoro. In other words, E can be phenyl, thienyl, benzothienyl, and napthyl, or a mono- or disubstituted derivative of phenyl, thienyl, benzothienyl, and napthyl, such as chlorophenyl, dichlorophenyl, chlorofluorophenyl, fluorophenyl, difluorophenyl, methylphenyl, dimethylphenyl, etc, chlorothienyl, dichlorothienyl, chlorofluorothienyl, fluorothienyl, difluorothienyl, methylthienyl, dimethylthienyl, etc, chlorobenzothienyl, dichlorobenzothienyl, chlorofluorobenzothienyl, fluorobenzothienyl, difluorobenzothienyl, methylbenzothienyl, dimethylbenzothienyl, etc, chloronaphthyl, dichloronaphthyl, chlorofluoronaphthyl, fluoronaphthyl, difluoronaphthyl, methylnaphthyl, dimethylnaphthyl, etc. These substituents may be in any reasonable position on the aromatic or heteroaromatic moiety. A person of ordinary skill in the art will understand that the number of substituents will be an integer.

In other embodiments, E is a moiety selected from the group consisting of phenyl, napthyl, and benzothienyl, or E is a monochloro derivative of one of these moieties, i.e. chlorophenyl, chloronaphthyl, or chlorobenzothienyl. These substituents may be in any position on the aromatic or heteroaromatic moiety.

A "pharmaceutically acceptable salt" is any salt that retains the activity of the parent compound and does not impart any additional deleterious or untoward effects on the subject to which it is administered and in the context in which it is administered compared to the parent compound.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

Compounds Comprising

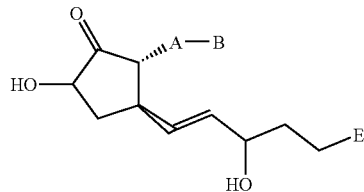

or a pharmaceutically acceptable salt or a prodrug thereof, are specifically contemplated herein.

Compounds Comprising

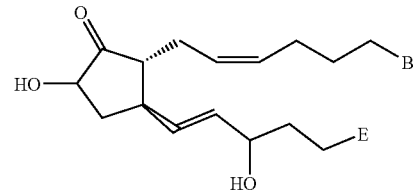

or a pharmaceutically acceptable salt or a prodrug thereof, are specifically contemplated herein.

Compounds Comprising

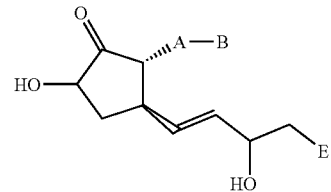

or a pharmaceutically acceptable salt or a prodrug thereof, are specifically contemplated herein.

Compounds Comprising

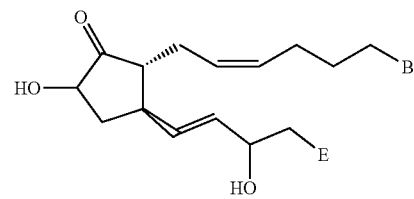

or a pharmaceutically acceptable salt or a prodrug thereof, are specifically contemplated herein.

Other Embodiments Comprise

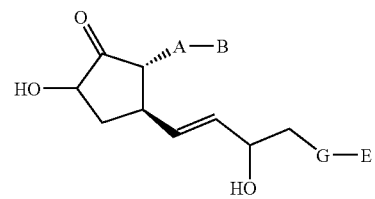

or a pharmaceutically acceptable salt or a prodrug thereof, wherein G is $CH_2$, O, or S.

Other Embodiments Comprise

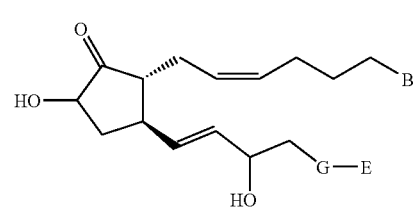

or a pharmaceutically acceptable salt or a prodrug thereof, wherein G is $CH_2$, O, or S.

Other Compounds Comprise

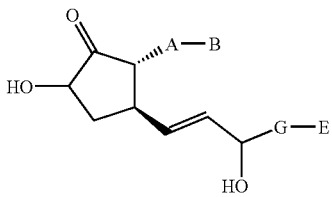

or a pharmaceutically acceptable salt or a prodrug thereof, wherein G is $CH_2$, O, or S.

Other Compounds Comprise

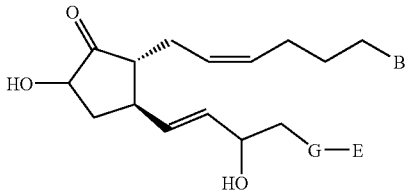

or a pharmaceutically acceptable salt or a prodrug thereof, wherein G is $CH_2$, O, or S.

Other Embodiments Comprise

In these embodiments, B and E have the meanings previously described.

Another Embodiment Comprises

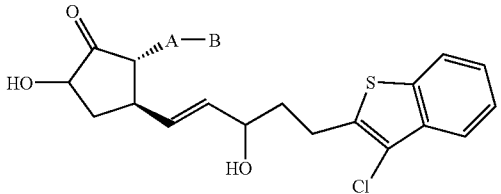

or a pharmaceutically acceptable salt or a prodrug thereof.

Another Embodiment Comprises

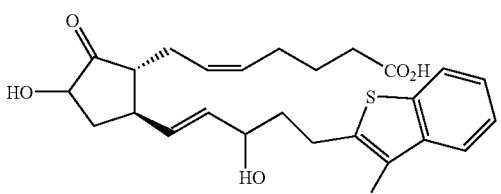

or a pharmaceutically acceptable salt or a prodrug thereof.

Another Embodiment Comprises

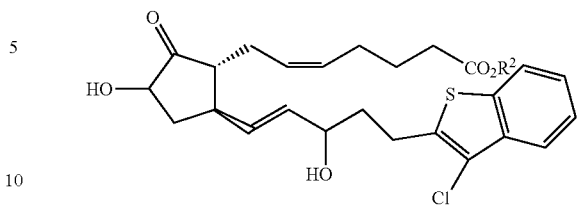

or a pharmaceutically acceptable salt or a prodrug thereof, wherein $R^2$ is an alkyl moiety having from 1 to 6 carbons.

Thus, R may be methyl, ethyl, propyl, isopropyl, butyl or an isomer thereof, pentyl or an isomer thereof, or hexyl or an isomer thereof.

Another embodiment comprises one the following compounds:

(Z)-7-{(1R,5R)-5-[(E)-5-(3-Chloro-benzo[b]thiophen-2-yl)-3-hydroxy-pent-1-enyl]-3-hydroxy-2-oxo-cyclopentyl}-hept-5-enoic acid methyl ester (high and low Rf methyl esters 8H, 8L), and (Z)-7-{(1R,5R)-5-[(E)-5-(3-Chloro-benzo[b]thiophen-2-yl)-3-hydroxy-pent-1-enyl]-3-hydroxy-2-oxo-cyclopentyl}-hept-5-enoic acid (high and low Rf acids, 9H, 9L).

The compounds of disclosed herein are useful for the prevention or treatment of glaucoma or ocular hypertension in mammals, or for the manufacture of a medicament for the treatment of glaucoma or ocular hypertension.

The compounds disclosed herein are also useful as selective agonists of prostaglandin $EP_4$ receptors. As such they are useful for the treatment of certain diseases or conditions, particularly those which are related to activity of a prostaglandin $EP_4$ receptor. While not intending to limit the scope of the invention in any way, or be bound in any way by theory, it is commonly believed in the art that prostaglandin $EP_4$ receptor activity is related to the following diseases or conditions, and as such, these diseases or conditions may be prevented or treated by prostaglandin $EP_4$ receptor agonists: asthma, dysmenorrhea, osteoporosis, bone disorders, constipation, renal disorders, sexual dysfunction, baldness, acute hepatitis, bronchitis, burn, chronic obstructive respiratory diseases, Crohn's disease, digestive ulcer, hemophagous syndrome, hepatopathy, hypercytokinemia at dialysis, hypertension, immunological diseases, inflammatory conditions, Kawasaki disease, liver injury, macrophage activation syndrome, myocardial ischemia, nephritis, nerve cell death, premature birth, pulmonary emphysema, pulmonary fibrosis, pulmonary injury, renal failure, sepsis, shock, sleep disorder, Still disease, stomatitis, systemic granuloma, systemic inflammatory syndrome, thrombosis and stroke, ulcerative colitis, acute myocardial infarction, vascular thrombosis, hypertension, pulmonary hypertension, ischemic heart disease, congestive heart failure, and angina pectoris.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

EXAMPLE 1

(Z)-7-{(1R,2R,3R)-3-(tert-Butyl-dimethyl-silanyloxy)-2-[(E)-3-(tert-butyl-dimethyl-silanyloxy)-5-(3-chloro-benzo[b]thiophen-2-yl)-pent-1-enyl]-5-oxo-cyclopentyl}-hept-5-enoic acid methyl ester (3). Iodide 1 was prepared according to the method described in U.S. Patent Application No. 365,369, filed Feb. 11, 2003, incorporated herein by reference. A −78° C. solution of iodide 1 (scheme 1, 2.305 g, 4.6 mmol) in THF (10 mL) was treated dropwise with t-butyl-lithium (5.9 mL, 10.0 mmol, 1.7 M/pentane). After stirring for 30 minutes, the red mixture was treated with lithium 2-thienylcyanocuprate (18.4 mL, 4.6 mmol, 0.25 M/THF, Aldrich). The resulting brown mixture was stirred in an ice bath for 10 minutes and then was cooled back down to −78° C. At this time, a solution of enone 2 (1.63 g, 4.6 mmol) in THF (5.0 mL) was added dropwise by cannula and the resulting mixture stirred for 30 minutes at −78° C., 30 minutes at 0° C. and then 30 min. at room temperature.

The reaction was quenched by addition of a solution of 10 mL concentrated $NH_4OH$ in 90 mL saturated $NH_4Cl$. The resulting mixture was stirred for 15 min. and was then extracted with ethyl acetate (3×100 mL). The combined ethyl acetate solution was dried ($MgSO_4$), filtered, and evaporated. Purification by flash chromatography on silica gel (10% ethyl acetate/hexanes) provided the title ketone 3 (1.781 g, 2.5 mmol, 54%).

(Z)-7-{(1R,2S)-2-[(E)-3-(tert-Butyl-dimethyl-silanyloxy)-5-(3-chloro-benzo[b]thiophen-2-yl)-pent-1-enyl]-5-oxo-cyclopent-3-enyl-hept-5-enoic acid methyl ester (4). A solution of ketone 3 (1.781 g, 2.5 mmol,) in acetic acid (24 mL)/$H_2O$ (12 mL)/THF (12 mL) was heated at 70° C. (bath temperature) for16 h. The solution was allowed to cool to room temperature and then was poured into 750 mL saturated $NaHCO_3$ solution. The mixture was extracted with ethyl acetate (4×200 mL) and the combined ethyl acetate solution was dried ($Na_2SO_4$), filtered and evaporated. Purification by flash chromatography on silica gel (50% ethyl acetate/hexanes) gave 0.686 g (1.5 mmol, 60%) of the deprotected version of alcohol. 4.

A solution of the deprotected alcohol in dichloromethane (8 mL) was treated with 2,6-lutidine (0.20 mL, 1.7 mmol) and TBSOTf (0.37 mL, 1.6 mmol). After 1 h, saturated $NaHCO_3$ was added and the resulting mixture extracted with dichloromethane (3×25 mL). The combined dichloromethane solution was washed with 1 M HCl (50 mL) and brine (50 mL) and then was dried ($Na_2SO_4$), filtered and evaporated. Purification by flash chromatography on silica gel (10% ethyl acetate/hexanes) gave the title enone 4 (706 mg, 1.2 mmol, 83%).

(Z)-7-{(1R,2R)-2-[(E)-3-(tert-Butyl-dimethyl-silanyloxy)-5-(3-chloro-benzo[b]thiophen-2-yl)-pent-1-enyl]-5-oxo-cyclopentyl}-hept-5-enoic acid methyl ester (5). A solution of enone 4 (145 mg, 0.25 mmol) in toluene (4 mL) was added to a −45° C. mixture of $[Ph_3PCuH]_6$ in toluene (4 mL), rinsing with 0.5 mL toluene. The mixture was allowed to stir for 1 h and then was allowed to warm to room temperature. After 19 h at room temperature, the reaction was quenched by addition of 15 mL saturated $NH_4Cl$ solution. The resulting mixture was extracted with ethyl acetate (3×15 mL) and the combined ethyl acetate solution was dried ($Na_2SO_4$), filtered and evaporated. Purification by flash chromatography on silica gel (7.5% ethyl acetate/ hexanes to 12.5%) gave ketone 5 (111 mg, 0.19 mmol, 76%).

(Z)-7-{(1R,5R)-5-[(E)-3-(tert-Butyl-dimethyl-silanyloxy)-5-(3-chloro-benzo[b]thiophen-2-yl)-pent-1-enyl]-2-trimethylsilanyloxy-cyclopent-2-enyl}-hept-5-enoic acid methyl ester (6, scheme 2). A solution of ketone 5 (59 mg, 0.10 mmol) in THF (2 mL) was added to a −78° C. solution of LDA (75 μL, 0.12 mmol, 1.6 M/cyclohexane) in THF (0.2 mL). After 15 minutes, a solution of TMSCl (0.16 mL, 1.3 mmol) and triethylamine (0.25 mL, 1.8 mL) in 4.4 mL THF was added by cannula. After 5 min. at −78° C., the reaction was allowed to warm to room temperature. The mixture was stirred for 20 min., was poured into 6 mL hexanes and then was filtered through celite, rinsing with 50% ethyl acetate/ hexanes. The filtrate was evaporated, taken into dichloromethane and filtered through glass wool. Evaporation of the filtrate gave the crude enol silane (32 mg, 0.047 mmol) which was used directly in the next step. Dimethyldioxirane (prepared according to Adam et. al. *J. Org. Chem.* 1987, 52, 2800). $NaHCO_3$ (12 g, 143 mmol) was added to a solution of acetone (11 mL, 150 mmol) in $H_2O$ (20 mL). The flask was equipped with a short path distillation apparatus and a 50 mL receiving flask (cooled to −78° C.). Oxone (25 g, 41 mmol) was added in one portion and a 180 torr vacuum was applied. After 15 min., gas evolution had slowed considerably with ca. 10 mL of ca. 0.1 M dimethyldioxirane solution being collected in the receiving flask. The solution was used directly in the next step.

(Z)-7-{(1R,5R)-5-[(E)-3-(tert-Butyl-dimethyl-silanyloxy)-5-(3-chloro-benzo[b]thiophen-2-yl)-pent-1-enyl]-3-hydroxy-2-oxo-cyclopentyl}-hept-5-enoic acid methyl ester (7). A −78° C. solution of the crude enol silane (from above) was treated with dimethyldioxirane solution (1.2 mL, ca. 0.1 M/acetone, prepared above). After 20 min., 10 mL saturated $NaHSO_3$ solution was added and the reaction allowed to warm to room temperature. Attempted extraction of the mixture with 15 mL dichloromethane resulted in an emulsion; however addition of 15 mL ethyl acetate allowed for facile layer separation. The aqueous layer was further extracted with ethyl acetate (2×15 mL) and the combined ethyl acetate solution was dried ($Na_2SO_4$), filtered and evaporated.

The residue was dissolved in 5 mL 5:1 THF/$H_2O$ and pyridinium p-toluenesulfonate (PPTs, 6 mg, 0.02 mmol) was added. After 20 min. more PPTs (14 mg, 0.05 mmol) was added. After another 20 min., 10 mL saturated $NaHCO_3$ Solution was added and the mixture was extracted with ethyl acetate (1×50 mL, 2×25 mL). The combined ethyl acetate solution was dried ($Na_2SO_4$), filtered and evaporated. Purification by flash chromatography on silica gel (30% ethyl acetate/hexanes) gave hydroxyl ketone 7 (9 mg, 0.015 mmol, 32% from 6).

(Z)-7-{(1R,5R)-5-[(E)-5-(3-Chloro-benzo[b]thiophen-2-yl)-3-hydroxy-pent-1-enyl]-3-hydroxy-2-oxo-cyclopentyl}-hept-5-enoic acid methyl ester 8. An acetonitrile (0.35 mL) solution of 7 (9 mg, 0.015 mmol) was treated with HF-pyridine (0.07 mL). The solution was allowed to stir for 2 h and then 20 mL of saturated $NaHCO_3$ solution was added. The mixture was extracted with dichloromethane (3×15 mL) and the combined dichloromethane solution dried ($Na_2SO_4$), filtered and evaporated. Purification by preparative thin layer chromatography (50% ethyl acetate/hexanes) gave two diastereomers of diol 8 (2 mg each, 0.004 mmol each, 27% for each).

(Z)-7-1(1R,5R)-5-[(E)-5-(3-Chloro-benzo[b]thiophen-2-yl)-3-hydroxy-pent-1-enyl]-3-hydroxy-2-oxo-cyclopentyl}-hept-5-enoic acid 9 (high Rf diastereomer). A mixture of 8 (2 mg, 0.004 mmol) and rabbit liver esterase (3 mg) in pH 7.2 phosphate buffer (0.5 mL) and acetonitrile (0.05 mL) were stirred overnight. The volatiles were co-evaporated with acetonitrile (2×25 mL) and the residue was purified by flash chromatography on silica gel (5% methanol/dichloromethane) to give acid 9 (1 mg, 0.002 mmol, 50%). 300 MHz $^1$H NMR ($CDCl_3$, ppm) δ 7.73 (2H, d, J=8.4 Hz) 7.5–7.3 (2H, m) 5.8–5.3 (4 H, m) 4.3–4.1 (2H, overlapping m) 3.1–3.0 (2H, m) 2.7–1.2 (16H, overlapping m).

The more polar diastereomer of 8 was hydrolyzed as above to give 9 (1 mg, 0.002 mmol, 50%). 300 MHz $^1$H NMR ($CDCl_3$, ppm) δ 7.74 (2H, d, J=7.9 Hz) 7.5–7.3 (2H, m) 5.7–5.4 (4H, m) 4.3–4.1 (2H, overlapping m) 3.1–3.0 (2 H, m) 2.7–1.2 (16H, overlapping m).

EXAMPLE 2

The biological activity of the compounds 1H and 1L, prepared as described in Example 1 was tested using the following procedures.

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl $PGF_{2\alpha}$ (5 nM) were performed in a 100 µl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H-] $PGE_2$ (specific activity 180 Ci mmol) was used as the radioligand for EP receptors. [$^3$H] 17-phenyl $PGF_{2\alpha}$ was employed for FP receptor binding studies. Binding studies employing $EP_1$, $EP_2$, $EP_4$ and FP receptors were performed in duplicate in at least three separate experiments. A 200 µl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-$PGE_2$, or 5 nM [$^3$H] 17-phenyl $PGF_{2\alpha}$ and non-specific binding determined with $10^{-5}$M of unlabeled $PGE_2$, or 17-phenyl $PGF_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3,4}$/Gqi5; hEP4/Gqs5; hFP; hIP; hTP), were cultured in 100 mm culture dishes in high-glucose DMEM medium containing 10% fetal bovine serum, 2 mM 1-glutamine, 250 µg/ml geneticin (G418) and 200 µg/ml hygromycin B as selection markers, and 100 units/ml penicillin G, 100 µg/ml streptomycin and 0.25 µg/ml amphotericin B.

(b) Calcium Signal Studies on the Flipr™

Cells were seeded at a density of $5\times10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 15 minutes of dye-loading in the dark, using the calcium-sensitive dye Fluo-4 AM at a final concentration of 2 µM, plates were washed four times with HBSS-HEPES buffer to remove excess dye leaving 100 µl in each well. Plates were re-equilibrated to 37° C. for a few minutes.

Cells were excited with an Argon laser at 488 nm, and emission was measured through a 510–570 nm bandwidth emission filter (FLIPR™, Molecular Devices, Sunnyvale, Calif.). Drug solution was added in a 50 µl volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2$ ($hEP_1$; $hEP_2$/Gqs5; $hEP_{3,4}$/Gqi5; hEP4/Gqs5); $PGF_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an $n \geq 3$.

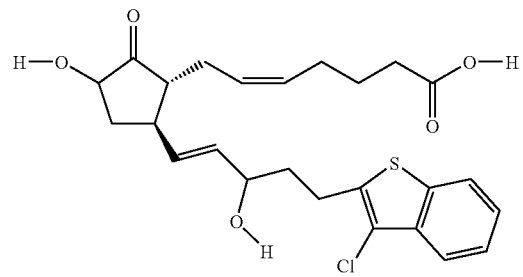

Compound 9H: High Rf diastereomer
Compound 9L: Low Rf diastereomer

| | BINDING (nm) | | | FUNCTIONAL (nm) | | | | | | |
|---|---|---|---|---|---|---|---|---|---|---|
| COMPOUND | HEP2 | HEP3D | HEP4 | HFP | HEP1 | HEP2 | HEP3A | HEP4 | HTP | HIP | HDP |
| 9H | NA | >10K | 170 | NA | NA | NA | NA | 53 | NA | NA | NA |
| 9L | NA | 8700 | 200 | NA | NA | NA | NA | 78 | >10K | NA | NA |

The results of the binding and activity studies presented in the table demonstrate that the compounds disclosed herein are selective prostaglandin EP$_4$ agonists, and are thus useful for the treatment of glaucoma, ocular hypertension, the other diseases or conditions disclosed herein. Further, while not intending to limit the scope of the invention in any way, or be bound in any way by theory, the 10-hydroxy substitution of the compounds disclosed herein are believed to provide additional stability relative to the analogous prostaglandin E compounds which have similar biological activity, and thus confer additional advantages.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound comprising

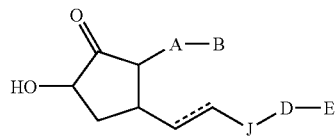

or a pharmaceutically acceptable salt or a prodrug thereof, wherein the dashed line represents the presence or absence of a double bond;

J is C=O or CHOH;

A is —(CH$_2$)$_6$—, or cis —CH$_2$CH=CH—(CH$_2$)$_3$—, wherein 1 or 2 carbons may be substituted with S or O;

B is CO$_2$H, or CO$_2$R, CONR$_2$, CONHCH$_2$CH$_2$OH, CON(CH$_2$CH$_2$OH)$_2$, CH$_2$OR, P(O)(OR)$_2$, CONRSO$_2$R, SONR$_2$, or

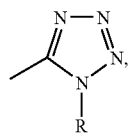

R is H, C$_{1-6}$ alkyl;

D is —(CH$_2$)$_n$—, —X(CH$_2$)$_n$, or —(CH$_2$)$_n$X—, wherein n is from 0 to 3 and X is S or O; and E is an aromatic or heteroaromatic moiety having from 0 to 4 substituents, said substituents each comprising from 1 to 6 non-hydrogen atoms.

2. The compound of claim 1 comprising

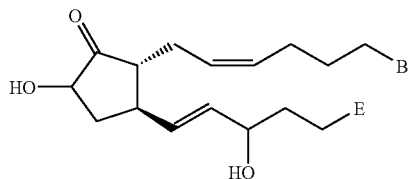

or a pharmaceutically acceptable salt or a prodrug thereof.

3. The compound of claim 2 wherein E is an aromatic moiety having from 0 to 2 substituents, wherein said aromatic moiety or heteroaromatic moiety is selected from the group consisting of phenyl, thienyl, benzothienyl, and napthyl, and said substituents are selected from the group consisting of methyl, methoxy, chloro, and fluoro.

4. The compound of claim 2 wherein E is a moiety selected from the group consisting of phenyl, napthyl, and benzothienyl, or E is a monochloro derivative of one of these moieties.

5. The compound of claim 1 comprising

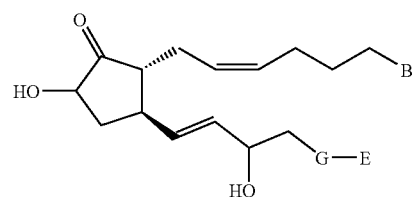

or a pharmaceutically acceptable salt or a prodrug thereof, wherein G is CH$_2$, O, or S.

6. The compound of claim 1 comprising

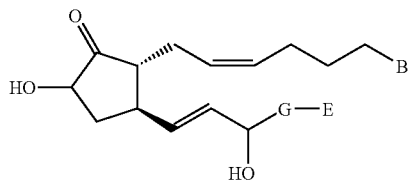

or a pharmaceutically acceptable salt or a prodrug thereof, wherein G is CH$_2$, O, or S.

7. The compound of claim 1 comprising

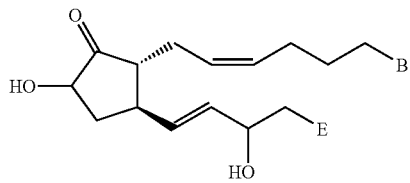

or a pharmaceutically acceptable salt or a prodrug thereof.

8. The compound of claim 1 comprising

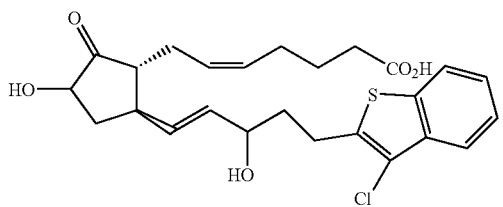

or a pharmaceutically acceptable salt or a prodrug thereof.

9. The compound of claim 1 comprising

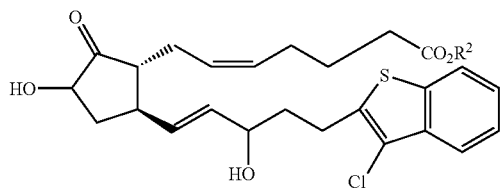

or a pharmaceutically acceptable salt or a prodrug thereof, wherein $R^2$ is an alkyl moiety having from 1 to 6 carbons.

10. A method comprising administering an effective amount of a compound to a mammal in need thereof for the treatment of glaucoma or ocular hypertension; said compound having a structure

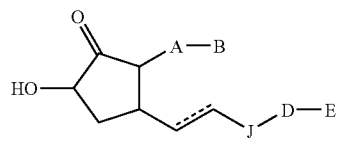

or a pharmaceutically acceptable salt or a prodrug thereof, wherein
the dashed line represents the presence or absence of a double bond;
J is C=O or CHOH;
A is —$(CH_2)_6$—, or cis —$CH_2CH$=$CH$—$(CH_2)_3$—, wherein 1 or 2 carbons may be substituted with S or O;
B is $CO_2H$, or $CO_2R$, $CONR_2$, $CONHCH_2CH_2OH$, $CON(CH_2CH_2OH)_2$, $CH_2OR$, $P(O)(OR)_2$, $CONRSO_2R$, $SONR_2$, or

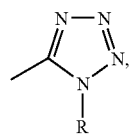

R is H, $C_{1-6}$ alkyl;
D is —$(CH_2)_n$—, —$X(CH_2)_n$, or —$(CH_2)_nX$—, wherein n is from 0 to 3 and X is S or O; and
E is an aromatic or heteroaromatic moiety having from 0 to 4 substituents, said substituents each comprising from 1 to 6 non-hydrogen atoms.

11. The method of claim 10 wherein A is cis-$CH_2CH$=$CH$—$(CH_2)_3$—.

12. The method of claim 10 wherein E is a phenyl, naphthyl, or benzothienyl moiety, or a monochloro derivative thereof.

13. The method of claim 10 comprising

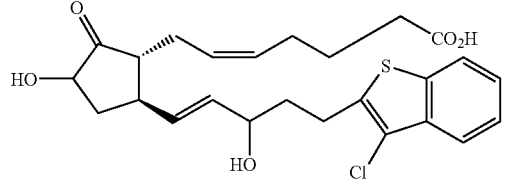

or a pharmaceutically acceptable salt or a prodrug thereof.

14. The method of claim 10 comprising

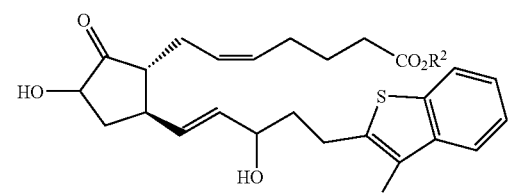

or a pharmaceutically acceptable salt or a prodrug thereof, wherein $R^2$ is an alkyl moiety having from 1 to 6 carbons.

15. A method comprising administering an effective amount of

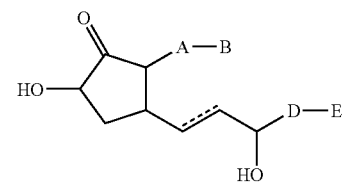

or a pharmaceutically acceptable salt or a prodrug thereof, to a mammal in need thereof for the treatment of a disease or condition,
wherein
the dashed line represents the presence or absence of a bond;
A is $(CH_2)_6$—, or cis —$CH_2CH$=$CH$—$(CH_2)_3$—, wherein 1 or 2 carbons may be substituted with S or O;
B is $CO_2H$, or $CO_2R$, $CONR_2$, $CONHCH_2CH_2OH$, $CON(CH_2CH_2OH)_2$, $CH_2OR$, $P(O)(OR)_2$, $CONRSO_2R$, $SONR_2$, or

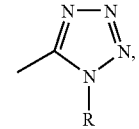

R is H, $C_{1-6}$ alkyl;
D is —$(CH_2)_n$—, —$X(CH_2)_n$, or —$(CH_2)_nX$—, wherein n is from 0 to 3 and X is S or O; and
E is an aromatic or heteroaromatic moiety having from 0 to 4 substituents, said substituents each comprising from 1 to 6 non-hydrogen atoms;

wherein said disease or condition is selected from the group consisting of asthma, dysmenorrhea, osteoporosis, bone disorders, constipation, renal disorders, sexual dysfunction, baldness, acute hepatitis, bronchitis, burn, chronic obstructive respiratory diseases, Crohn's disease, digestive ulcer, hemophagous syndrome, hepatopathy, hypercytokinemia at dialysis, hypertension, immunological diseases, inflammatory conditions, Kawasaki disease, liver injury, macrophage activation syndrome, myocardial ischemia, nephritis, nerve cell death, premature birth, pulmonary emphysema, pulmonary fibrosis, pulmonary injury, renal failure, sepsis, shock, sleep disorder, Still disease, stomatitis, systemic granuloma, systemic inflammatory syndrome, thrombosis and stroke, ulcerative colitis, acute myocardial infarction, vascular thrombosis, hypertension, pulmonary hypertension, ischemic heart disease, congestive heart failure, and angina pectoris.

16. The method of claim 15 wherein A is —(CH$_2$)$_6$— or cis-CH$_2$CH═CH—(CH$_2$)$_3$— having no heteroatom substitution.

17. The method of claim 15 comprising

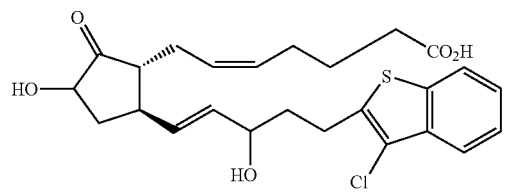

or a pharmaceutically acceptable salt or a prodrug thereof.

18. A method comprising administering an effective amount of

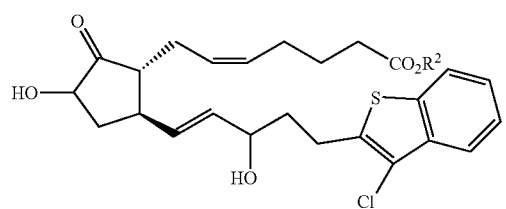

or a pharmaceutically acceptable salt or a prodrug thereof, to a mammal suffering from a disease or condition,
wherein R$^2$ is an alkyl moiety having from 1 to 6 carbons, and
said disease or condition is selected from the group consisting of asthma, dysmenorrhea, osteoporosis, bone disorders, constipation, renal disorders, sexual dysfunction, baldness, acute hepatitis, bronchitis, burn, chronic obstructive respiratory diseases, Crohn's disease, digestive ulcer, hemophagous syndrome, hepatopathy, hypercytokinemia at dialysis, hypertension, immunological diseases, inflammatory conditions, Kawasaki disease, liver injury, macrophage activation syndrome, myocardial ischemia, nephritis, nerve cell death, premature birth, pulmonary emphysema, pulmonary fibrosis, pulmonary injury, renal failure, sepsis, shock, sleep disorder, Still disease, stomatitis, systemic granuloma, systemic inflammatory syndrome, thrombosis and stroke, ulcerative colitis, acute myocardial infarction, vascular thrombosis, hypertension, pulmonary hypertension, ischemic heart disease, congestive heart failure, and angina pectoris.

19. The compound of claim 1 comprising
(Z)-7-{(1R,5R)-5-[(E)-5-(3-Chloro-benzo[b]thiophen-2-yl)-3-hydroxy-pent-1-enyl]-3-hydroxy-2-oxo-cyclopentyl}-hept-5-enoic acid methyl ester; or
(Z)-7-{(1R,5R)-5-[(E)-5-(3-Chloro-benzo[b]thiophen-2-yl)-3-hydroxy-pent-1-enyl]-3-hydroxy-2-oxo-cyclopentyl}-hept-5-enoic acid.

20. The compound of claim 9 wherein R$^2$ is methyl.

21. The compound of claim 1 comprising

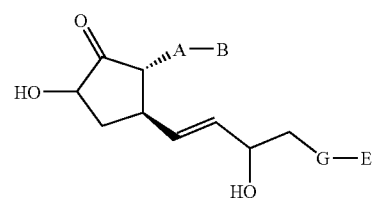

or a pharmaceutically acceptable salt or a prodrug thereof, wherein G is CH$_2$, O, or S.

22. The compound of claim 1 comprising

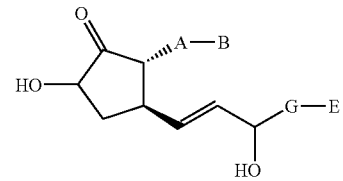

or a pharmaceutically acceptable salt or a prodrug thereof, wherein G is CH$_2$, O, or S.

23. The compound of claim 1 comprising

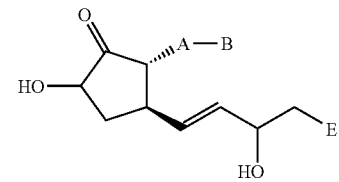

or a pharmaceutically acceptable salt or a prodrug thereof.

24. The compound of claim 1 comprising

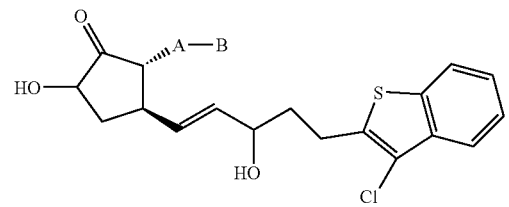

or a pharmaceutically acceptable salt or a prodrug thereof.

* * * * *